US00PP20113P2

(12) United States Plant Patent
Klemm

(10) Patent No.: US PP20,113 P2
(45) Date of Patent: Jun. 23, 2009

(54) ***PETUNIA* PLANT NAMED 'KLEPH07140'**

(50) Latin Name: ***Petunia* hybrid**
Varietal Denomination: KLEPH07140

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/082,036

(22) Filed: Apr. 7, 2008

(51) Int. Cl.
*A01H 5/00* (2006.01)

(52) U.S. Cl. ..... Plt./356
(58) Field of Classification Search ..... Plt./356
See application file for complete search history.

*Primary Examiner*—Susan B. McCormick Ewoldt
(74) *Attorney, Agent, or Firm*—Jondle & Associates, P.C.

(57) ABSTRACT

A new cultivar of *Petunia* particularly characterized by a compact and mounding growth habit, white flowers, continuous flowering and very floriferous, and good tolerance to rain and wind is disclosed.

1 Drawing Sheet

Genus and species: *Petunia* hybrid.
Variety denomination: 'KLEPH07140'.

BACKGROUND OF THE NEW PLANT

The present invention comprises a new and distinct cultivar of *Petunia*, botanically known as *Petunia* hybrid, and hereinafter referred to by the cultivar name 'KLEPH07140'. 'KLEPH07140' was discovered as a seedling resulting from a cross conducted in summer 2004 in Stuttgart, Germany between the proprietary female *Petunia* parent, 'W 214' (unpatented) and the proprietary male *Petunia* parent, 'J 501' (unpatented). A single plant selection was subsequently chosen for further evaluation and for asexual propagation.

The new cultivar was created in 2004 in Stuttgart, Germany and has been asexually reproduced repeatedly by vegetative cuttings and in-vitro propagation in Stuttgart, Germany over a three year period (more than 35 generations). 'KLEPH07140' has been found to retain its distinctive characteristics through successive asexual propagations.

Plant Breeder's Rights for this cultivar were applied for in Switzerland on Jul. 6, 2007. 'KLEPH07140' has not been made publicly available more than one year prior to filing of this application.

SUMMARY OF THE INVENTION

The following are the most outstanding and distinguishing characteristics of this new cultivar when grown under normal commercial practices in a greenhouse in Stuttgart, Germany.

1. Compact and mounding growth habit;
2. White flowers;
3. Continuous flowering and very floriferous; and
4. Good tolerance to rain and wind.

DESCRIPTION OF THE PHOTOGRAPH

This new *Petunia* plant is illustrated by the accompanying photograph which shows flowers, flower buds and foliage; the colors shown are as true as can be reasonably obtained by conventional photographic procedures. The photograph is of a plant about 5-months old and grown from rooted cuttings in an 11-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPH07140'. The data which define these characteristics were collected from asexual reproductions carried out in Stuttgart, Germany. The plant history was taken on 5-month-old plants in 11-cm pots that were pinched once approximately one week after potting and grown in a greenhouse in the spring. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Solanacea.
- *Genus and species.*—*Petunia* Hybrid.
- *Common name.*—*Petunia*.

Parentage:
- *Female parent.*—The proprietary *Petunia* parent, 'W 214' (unpatented).
- *Male parent.*—The proprietary *Petunia* parent, 'J 501' (unpatented).

Plant:
- *Form.*—Compact.
- *Habit.*—Mounding.
- *Height (from top of soil).*—11.0 cm.
- *Width (horizontal plant diameter).*—17.0 cm.
- *Propagation.*—Vegetative propagation by cuttings or in vitro propagation.
- *Time to produce a finished flowering plant.*—13 weeks.
- *Time to initiate and develop roots.*—18 days.
- *Root description.*—Moderate density and moderate branching, white roots.

Stems:
- *Average number (basal).*—6.
- *Length of basal branches (from the base of the stem to the tip).*—9.0 cm.

*Internode length.*—0.5 cm to 2.5 cm.
*Diameter of branches* (*from midpoint*).—1.5 cm to 6.0 cm.
*Stem color.*—RHS 137C.
*Anthocyanin.*—Absent.
*Texture.*—Smooth.

Leaves:
*Arrangement.*—Alternate.
*Size.*—Length: 1.0 cm to 4.0 cm. Width: 0.5 cm to 3.5 cm.
*Shape.*—Elliptic.
*Margin.*—Weak undulation.
*Apex.*—Acute.
*Base.*—Obtuse.
*Immature leaf.*—Color: Upper surface: RHS 138A. Lower surface: RHS 138C.
*Mature leaf.* Color: Upper surface: RHS 146A. Lower surface: RHS 146B.
*Texture.*—Smooth.
*Venation.*—Pinnate.
*Venation color.*—Upper surface: RHS 145A. Lower surface: RHS 145B.
*Petioles.*—Length: 0.2 cm to 3.0 cm. Diameter: 0.3 cm. Color (both upper and lower parts): RHS 138B. Texture: Smooth.

Flower bud:
*Shape.*—Irregular to oblong.
*Size.*—Length: 4.0 cm. Diameter: 1.0 cm.
*Color at tight bud.*—RHS 154D.
*Immature flower color.*—RHS 155B.
*Texture.*—Pubescent.

Inflorescence:
*Blooming habit* (*flowering season*).—Continuous flowering during the summer.
*Inflorescence type.*—Single flower.
*Number of flowers per node.*—1.
*Lastingness of individual blooms on the plant.*—7 days.
*Fragrance.*—Absent.
*Pedicels.*—Color: RHS 137C. Length: 1.8 cm. Diameter: 0.3 cm.
*Texture.*—Smooth.

Flowers:
*Shape.*—Cup-shaped.
*Size.*—Diameter (flower face): 4.5 cm. Depth (total length of flower): 3.0 cm. Funnel: Length: 2.5 cm. Diameter (at opening): 0.7 cm. Outside texture: Smooth.
*Mature flower.*—Face/Margin Color (both surfaces): RHS 155B. Corolla tube: Color inside (throat): RHS 155B. Color outside: RHS 155B. Petals: Apex: Rounded to emarginate. Base: Reniform. Margin: Undulating. Waviness: Moderate. Lobation: Weak. Texture: Smooth.
*Calyx arrangement.*—One star-shaped calyx tube with five sepals fused at the base per flower.
*Sepals.*—Number: 5. Color: RHS 138A. Length: 1.8 cm. Width: 0.4 cm. Shape: Lanceolate to elliptic. Apex: Obtuse. Base: Fused. Margin: Entire. Texture: Smooth.

Reproductive organs:
*Stamens.*—Quantity: 5. Shape: Needlelike with elliptic head. Filament: Length: 0.5 cm. Diameter: 0.1 cm. Color: RHS 150A. Anther: Shape: Elliptic. Color: RHS 4D. Length: 0.3 cm. Diameter: 0.2 cm. Pollen: Color: RHS 4D. Amount: Moderate.
*Pistils.*—Number: 1. Length: 0.4 cm. Diameter: 0.1 cm. Stigma: Color: RHS 150A. Shape: Oval. Length: 1.9 cm. Diameter: 0.1 cm. Style: Color: RHS 150C. Length: 2.0 cm. Diameter: 0.1 cm. Texture: Fibrous.

Fruit and seed set: None observed.
Disease and insect resistance: Not observed.

COMPARISON WITH PARENTAL AND COMMERCIAL CULTIVARS

'KLEPH07140' differs from the female parent, the proprietary *Petunia* 'W 214' (unpatented) in that 'KLEPH07140' has a compact and mounding growth habit, while 'W 214' has a spreading growth habit.

'KLEPH07140' differs from the male parent, the proprietary *Petunia*'J 501' (unpatented) in that 'KLEPH07140' has a compact and mounding growth habit, while 'J 501' has an upright growth habit.

'KLEPH07140' differs from the commercial comparison variety 'Charming White' (unpatented) in that 'KLEPH07140' is tolerant to rain and wind, while 'Charming White' is sensitive to rain and wind.

I claim:

1. A new and distinct cultivar of *Petunia* plant as shown and described herein.

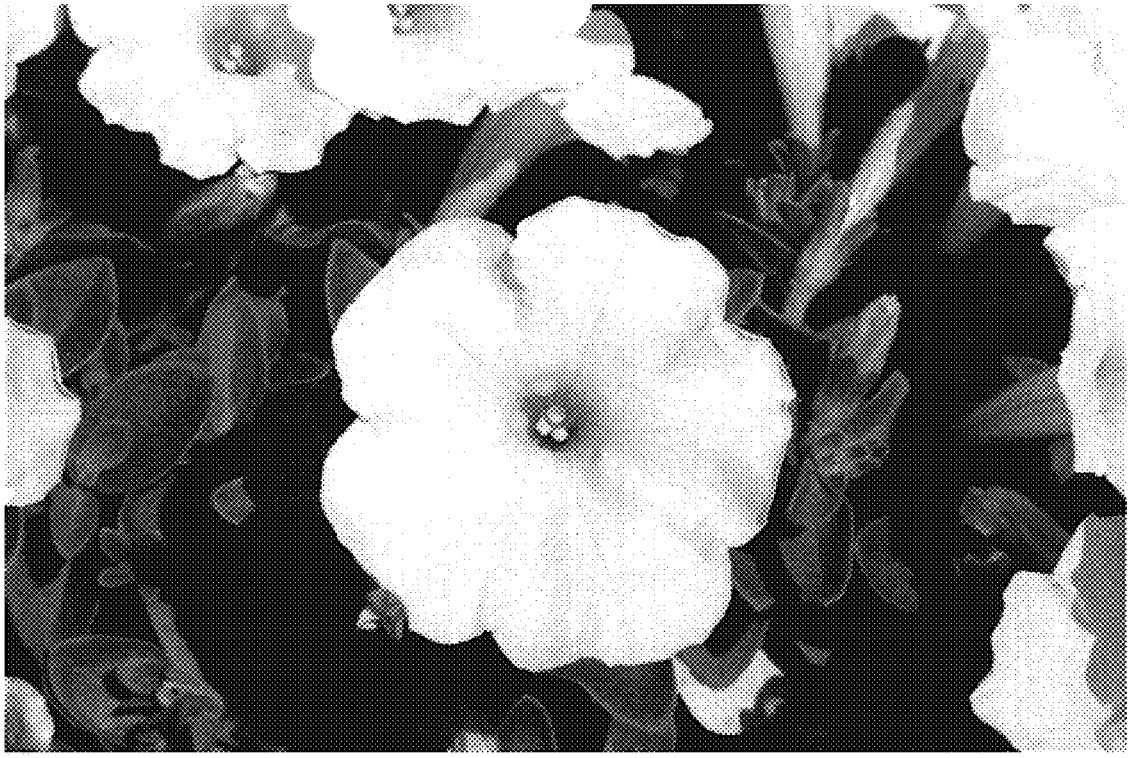

* * * * *